US007592002B2

(12) United States Patent
Gupta

(10) Patent No.: US 7,592,002 B2
(45) Date of Patent: Sep. 22, 2009

(54) SUGAR ESTERS FOR DEPILATION (HAIR REMOVAL), DEMABRASION, AND WRINKLES REDUCTION

(75) Inventor: Shyam K Gupta, Scottsdale, AZ (US)

(73) Assignee: Bioderm Research, Scottsdale, AZ (US)

( * ) Notice: Subject to any disclaimer, the term of this patent is extended or adjusted under 35 U.S.C. 154(b) by 513 days.

(21) Appl. No.: 11/163,779

(22) Filed: Oct. 31, 2005

(65) Prior Publication Data

US 2007/0098663 A1    May 3, 2007

(51) Int. Cl.
*A61K 8/73* (2006.01)
*A61K 31/74* (2006.01)
(52) U.S. Cl. ............... 424/70.13; 424/78.03; 424/78.08
(58) Field of Classification Search ........................ None
See application file for complete search history.

(56) References Cited

U.S. PATENT DOCUMENTS

2003/0027924 A1* 2/2003 Fahy et al. ..................... 525/7
2006/0252804 A1* 11/2006 Pieroth et al. ............... 514/352

FOREIGN PATENT DOCUMENTS

JP        11060928 A  *  3/1999
WO    WO 02085322 A  *  10/2002

OTHER PUBLICATIONS

Machine English Translation of JP 11060928 A.*

* cited by examiner

*Primary Examiner*—Michael G Hartley
*Assistant Examiner*—Paul Dickinson

(57) ABSTRACT

This invention relates to the preparation of conjugates of sucrose and certain polyhydroxy lactones. Such conjugates have shown surprising and unexpected adhesive properties, which are useful for certain cosmetic applications such as dermabrasion, topical exfoliation, age spot removal, wart removal, and hair removal (depilation).

9 Claims, 1 Drawing Sheet

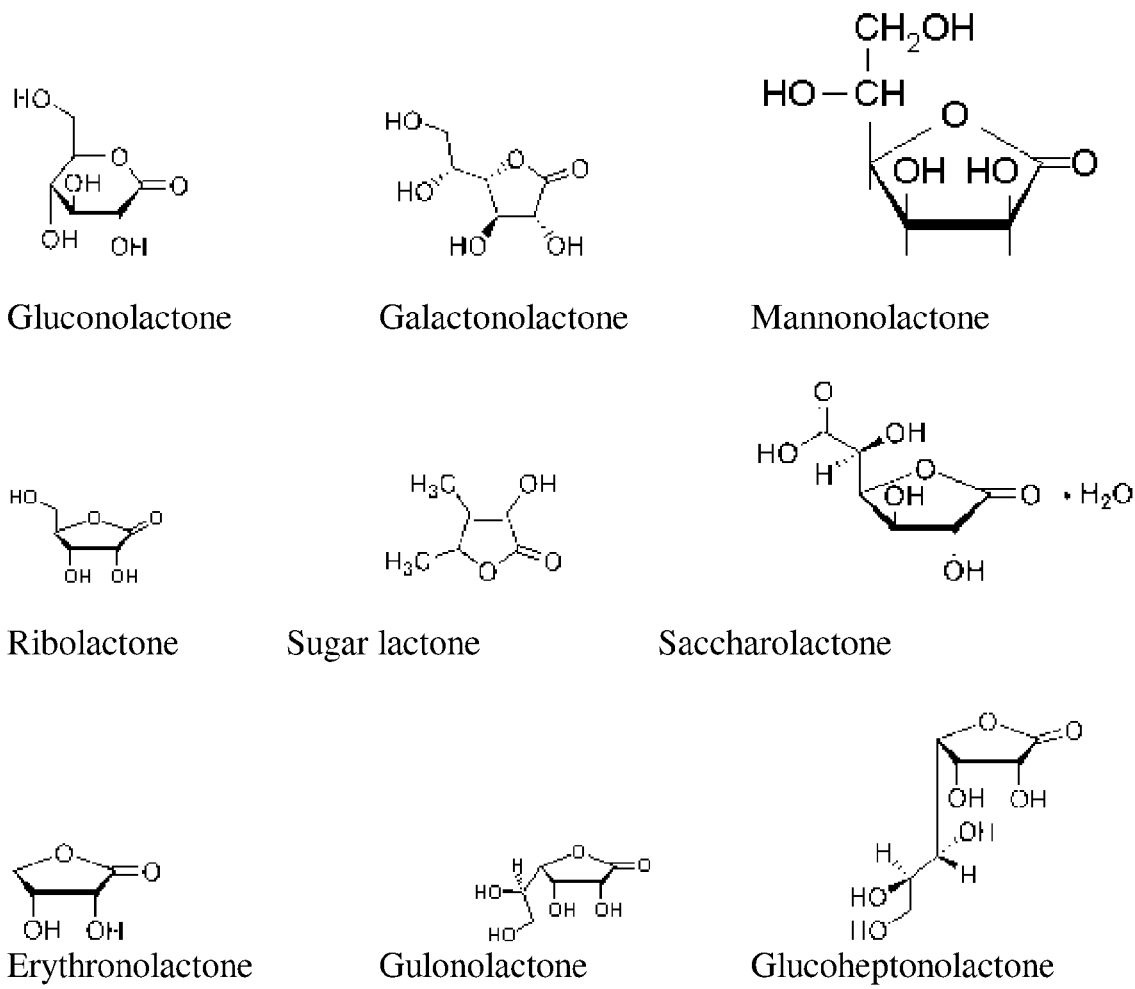
Figure 1. Chemical Structure of Hydroxy and Polyhydroxy Lactones

SUGAR ESTERS FOR DEPILATION (HAIR REMOVAL), DEMABRASION, AND WRINKLES REDUCTION

This invention relates to the preparation of conjugates of sucrose and certain polyhydroxy acid lactones, also known as polyhydroxy lactones, and certain polyhydroxy acids that can exist in equilibrium with their polyhydroxy lactone structure forms. Such conjugates have now shown surprising and unexpected adhesive properties, which are useful for certain cosmetic applications of great commercial and consumer interest, such as dermabrasion, topical exfoliation, age spot removal, wart removal, and hair removal (depilation).

Sugar based compositions have well known cosmetic applications. For example, sugar and water mixtures have been used for cosmetic depilatory applications for the removal of hair on human skin surface. Some of the prior art examples include; British Letters Pat. No. 1,242,083 (Doughty) discloses the combination of sugar with citric acid and water in the formation of a paste that can be used as a depilatory or hair removal composition. EP0018668 (Kasidecioglu) disclose a mixture of sugar, water, a weak acid and a resin, with the composition 100 parts by weight of sugar, 18 to 20 parts by weight of water, 2 to 6 parts by weight of gum arabic, and 0.2 to 0.4 part by weight of citric acid, tartaric acid or another physiologically acceptable acid suitable for hair removal. DE10208148 (Hagemann) discloses a paste composition comprising of freshly pressed lemon juice 32.25%, melted sugar 64.50%, and water 3.25%. The mixture is heated to produce a viscous mass. Since lemon juice is about 91% by weight of water, the actual amount of water in this composition is much higher than 3.25%. Such pastes are useful for hair removal. CA2289879 (Brynczka) discloses a composition that is comprised of sugar, corn syrup, cornstarch, citric acid and water or equivalent ingredients, which produce a pliable, wax-like consistency that adheres to, and removes hair from the skin surface. GB2336536 (Guillaume et al.) discloses a gum like composition that is prepared by heating an aqueous solution of sucrose (60-90% by weight) in the presence of citric or hydrochloric acid and polyethylenimine catalyst. GB2336535 (Guillaume et al.) discloses a paste composition that is prepared by heating an aqueous solution of sucrose (60-90% by weight) in the presence of citric or hydrochloric acid and optionally a polyethylenimine catalyst until it is substantially free of sucrose and then adding a natural wax or resin. DE4229392 (Hassoun) discloses a composition for mechanical removal of body hair that is made by boiling a mixture of 580-620 parts by weight of sugar, 80-100 parts by weight of distilled water and 0.7-1.1 parts by weight of citric acid. Boiling is continued for a period such that when cooled to room temperature a brushable paste with a honey-like consistency is obtained. FR2692144 (Brun) discloses a depilatory composition to pull out the hairs, comprising a cooked mixture of sugar and vinegar. U.S. Pat. No. 5,158,765 (Qasem) discloses a composition for the removal of hair that is composed of a mixture of sugar, water and aspirin. Among other similar sugar-based compositions, U.S. Pat. No. 5,698,187 (Naggiar) discloses a composition for the removal of hair from the human body that is composed of a mixture of maltodextrin, sucrose, water and citric acid. This mixture is heated to dissolve the solute materials, and then cooled to form a soft, pliant composition that can be manually applied to the skin. U.S. Pat. No. 4,842,610 (Gordon et al.) discloses adhesive compositions that comprise 90 to 99.5% corn syrup and 0.5% to 10% added water by weight. U.S. Pat. No. 4,832,949 (Royal) discloses a depilatory composition that is made up of a mixture of honey, sugar and citric acid, which mixture is heated to a predetermined temperature level, then allowed to cool so as to form a highly viscous, wax-like composition which can be applied manually in slender strips to the skin. British Letters Patent No. 901,624 (Wenden) discloses the formulation of a cream made up of sugar and lemon juice, glycerin, boric acid powder, sodium chloride and a water carrier. These ingredients are heated, and then allowed to cool to a temperature at which they may be poured into separate jars or containers, and specifically are heated to a temperature on the order of 278 F. to form a plastic mass.

However, it is commonly recognized that the above-mentioned sugar-based compositions do not possess consistent adhesive properties. Moreover, such compositions that are based on sugar and/or ingredients that contain substantial amount of sugar or sugar derivatives, such as honey or corn syrup, also contain substantial amounts of water, or alcohol, or mixtures of water and alcohol, which tend to evaporate each time a bottle is opened for product application, thus resulting in the crystallization of sugar or sugar derivatives from such compositions. Such crystallizations cause a loss of the adhesive power of such compositions, and also make it harder for the bottle to be opened for product use. U.S. Pat. No. 6,417,346 (Salome et al.) further discusses such sugar crystallization problems. Additionally, a "dry-down" period is required for such sugar and sugar derivatives based compositions after product applications to let water or alcohol partially evaporate to increase their adhesive power. This "dry-down" period can be from 5 minutes to 20 minutes, or even longer. Thus, the product does not gain sufficient "stickiness" to effectively remove hair if this "dry-down" period is not observed in depilatory applications of such compositions. Sugar based adhesive compositions are also known to be non-coatable on sheets or strips, which is a major disadvantage (Spina et al., U.S. Patent application ser. No. 20030004522).

Sugar based adhesive compositions for dermabrasion; topical exfoliation, wart removal, or depilatory applications are easily washed-off from skin after their application, if any residues still remain on the skin after such applications. This single benefit is still one of the most desirable features of sugar-based depilatory compositions. Nad's sugar based depilatory gels, which are currently most popular compositions in consumer market, are reported to contain a mixture of honey, molasses, fructose, vinegar, lemon juice, water, alcohol and food dye. Although these compositions work well for hair removal, they tend to dry-up and develop crystals of unknown composition, as the jars are opened during their use due to the loss of water and alcohol from such compositions. The formation of such crystals then makes such compositions ineffective for hair removal. The same problem is experienced with the commercially available compositions that are based solely on mixtures of sucrose, water, and citric acid. Moreover, the preparation of such sugar and citric acid based compositions requires extended, yet unspecified periods of heating at higher temperatures. For example, U.S. Pat. No. 4,832,949 (Royal) discloses that heating is required for extended periods at temperatures ranging from 245 F. to 300 F. This frequently results in compositions that are highly discolored or inconsistent from batch to batch, thus resulting in variable performance for hair removal.

The adhesive properties of sugar and water mixtures are thus well known in the prior art. However, such sugar and water based compositions are not reliable, as they can crystallize upon their storage, and their adhesive property is highly variable from batch to batch. Sucrose and water based adhesive compositions do have the advantage of a water cleanup procedure. It would thus be advantageous if an adhesive composition based on sucrose and water can be made with the following properties: (1) It can be made such that the adhesive properties of sucrose are increased substantially and reproducibly, (2) The amount of water used is minimized to avoid crystallization of sucrose, (3) It is applied cold without requiring any pre-heating step, and (4) It is washable with water, and (5) No dry-down period is required, (6) complete depilation is achieved in a single application, and (7) The preparation of compositions is reasonably uniform from batch to batch under less harsh manufacturing conditions.

It has now been discovered, surprisingly and unexpectedly, that the adhesive properties of sucrose and water mixtures can be further increased substantially by combining sucrose with a polyhydroxy lactone or a polyhydroxy acid that can also exist in its lactone form in equilibrium with the acid form, under the conditions of the present invention, which results in the formation of a sucrose—polyhydroxy lactone conjugate. This sucrose—polyhydroxy lactone conjugate is substantially higher in adhesive properties, compared to sugar and water based compositions, yet it is water-soluble. The present invention is thus based on: (1) sucrose, (2) a minimum amount of water to solubilize sucrose, and (3) a conjugating agent, such as a Polyhydroxy lactone, or a polyhydroxy acid that can also exist in its lactone form in equilibrium with the acid form. Also surprisingly and unexpectedly, such conjugates of sucrose and Polyhydroxy lactone, or a polyhydroxy acid that can also exist in its lactone form in equilibrium with the acid form, do not develop crystallization upon storage. Optionally, a water soluble hydroxylic or polyhydroxyl solvent can be included to improve the rheology, stability, and cosmetic benefits of such sucrose—polyhydroxy lactone conjugate based adhesive compositions. The aforementioned addition of a water-soluble hydroxylic or polyhydroxyl solvent further inhibits sugar crystallization problems. Also optionally, hair growth retardant, skin soothing, anti-irritant, topical analgesic, antioxidant, UV absorber, or other such skin or hair beneficial agents or compositions can also be included.

The ratio of sugar to Polyhydroxy lactone, or a polyhydroxy acid that can also exist in its lactone form in equilibrium with the acid form is from 100:1 to 1:1. The adhesive power increases as the amount of Polyhydroxy lactone, or a polyhydroxy acid that can also exist in its lactone form in equilibrium with the acid form is increased up to a certain optimal level. This optimal level is determined by actual experimentation, as any additional ingredients that are also included can significantly affect the adhesive property of such compositions.

Gupta (U.S. patent application Ser. No. 11/162,209) discloses an adhesive composition that is based on sucrose crosslinked with a multi-dentate molecule, such as polyphosphoric acid, or a derivative of polyphosphoric acid, such as phytic acid. However, such crosslinked derivatives of sucrose with Polyphosphoric acid or a derivative of polyphosphoric acid are distinctly different from the compositions of the present invention. The present invention is even more surprising and unexpected in view of Gupta teachings.

Sucrose is the most common, and most cost effective, ingredient in the compositions of the present invention. However, other monosaccharides and disaccharides, and the compositions that contain said saccharides such as corn syrup or honey can also be used either alone or in combination with each other, including sucrose. Monosaccharides and disaccharides are simple sugars of chemical carbohydrate group. Monosaccharide is the simplest sugar. Simple sugars can contain a chain of from four to seven carbon atoms. Such sugars are called tetroses, pentoses, hexoses, and heptoses, respectively. The examples include erythrose, threose, Arabinose, Ribose, Ribulose, Xylose, Xylulose, Lyxose, Allose, Altrose, Fructose, Glucose, Galactose, Gulose, Idose, Mannose, Sorbose, Talose, Tagatose, and Sedoheptulose. Two simple sugars combine to form a disaccharide. The examples of disaccharide include sucrose, lactose, maltose, and trehalose. Of these, only hexoses, and all of disaccharides, are most useful as adhesive agents. Natural or chemical processes can be used to convert monosaccharides into compounds that retain the basic configuration of saccharides, but have different functional groups. Sugar alcohols are, for example, made by the hydrogenation of sugars that have an aldehyde or a ketone group. For example, sorbitol is made by the hydrogenation of glucose. Erythrose and Xylose are similarly converted by hydrogenation into erythritol and xylitol, respectively.

The hydroxylic or polyhydroxyl solvent is selected from diglycerol, polyglycerol, triglycerol, tetraglycerol, pentaglycerol, hexaglycerol, glycerin, polyethylene glycol, propylene glycol, butylene glycol, methylpropanediol, ethoxydiglycol, and combinations thereof.

The preferred sucrose-conjugating agent is Gluconolactone, also known as Glucono-delta-lactone. Other polyhydroxy lactones, or a polyhydroxy acid that can also exist in its lactone form in equilibrium with the acid form that can be used include erythronolactone, Isocitric acid lactone, glucooctanolactone, galactonolactone, gulonolactone, sugar lactone, mannonolactone, saccharolactone, glucoronolactone, and ribolactone, and their corresponding acid forms. The acid form of gluconolactone, for example, is gluconic acid. The chemical structures of some of which are shown in FIG. 1.

FIG. 1.

The exact chemical mechanism of how or why the adhesive power of sucrose is increased by its conjugation with a hydroxy or polyhydroxy lactone is not known at this time. It is speculated by the present inventor that sucrose molecule has multiple hydroxyl groups, and some of these hydroxy groups undergo a chemical reaction of trans-esterification with the lactone moiety of polyhydroxy lactone to form monomers or polymers of sucrose polyhydroxy acid esters. This process can thus also occur with polyhydroxy acids that can exist in equilibrium with their polyhydroxy lactone form. The progress of this conjugation process was established by infra-red (ir) spectroscopy. The ir spectrum showed the disappearance of the lactone absorption band and the appearance of an ester absorption band when a polyhydroxy lactone, for example, gluconolactone, is conjugated with sucrose. Irrespective of the actual mechanism of conjugation process, the surprising and unexpected discovery of superior adhesive property of such sucrose polyhydroxy lactone conjugates and their cosmetic applications, for example in hair removal (depilation) are the focal features of the present invention.

Although the compositions of the present invention do not cause irritation or pain during depilation process, it may be desirable to include skin cooling and skin numbing agents for some consumers who have delicate, sensitive skin. The examples of such ingredients that can be selected for this purpose includes, but not limited to, menthol, menthol esters, methyl salicylate, camphor, benzocaine, dibucaine, dyclonine, lidocaine, pramoxine, tetracaine, ephedrine, epinephrine, phenylephrine, and their derivatives, and combinations thereof.

The usual ingredients to adjust the pH of the compositions of present invention, for example citric acid, lactic acid, tartaric acid, gluconic acid, Mandelic acid, Salicylic acid, ascorbic acid, hydrochloric acid, sulfuric acid, phosphoric acid, and various resins in their acid form (H ion form) such as Divinylbenzene/methacrylic acid copolymer and Polysulfonic acid, to better match skin pH can also be included.

The rheology of the compositions of the present invention can be modified by including one or more alternate rheological modifiers. The rheological modifiers that can be used in this invention include high molecular weight crosslinked homopolymers of acrylic acid, and Acrylates/C10-30 Alkyl Acrylate Crosspolymer, such as the Carbopol. and Pemulen series, both available from B. F. Goodrich, Akron, Ohio, USA; anionic acrylate polymers such as Salcare and cationic acrylate polymers such as Salcare SC96, available from Ciba Specialties, High Point, N.C., USA; Acrylamidopropyltrimonium chloride/acrylamide; Hydroxyethyl methacrylates polymers, Steareth-10 Allyl Ether/Acrylate Copolymer; Acrylates/Beheneth-25 Methacrylate Copolymer, known as Aculyn, available from International Specialties, Wayne, N.J., USA; Glyceryl Polymethacrylate, Acrylates/Steareth-20 Methacrylate Copolymer; bentonite; gums such as alginates, carageenan, gum acacia, gum arabic, gum ghatti, gum karaya, gum tragacanth, guar gum; guar hydroxypropyltrimonium chloride, xanthan gum, gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol (PVA), PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent, and most preferably from 0.1 to 2 weight percent.

Additional cosmetic compositions can also be made by the present disclosure. Depilatory clay, for example, can be made by the inclusion of from 0.1 to 10% by weight, or even more, of suitable clay, such as bentonite, montmorillonite, zeolite, alumina, silicates, and such.

The cosmetically acceptable composition of this invention may include one or more preservatives. Example of preservatives, which may be used include, but are not limited to 1,2-dibromo-2,4-dicyano butane (Methyidibromo Glutaronitrile, known as MERGUARD. Nalco Chemical Company, Naperville, Ill., USA), benzyl alcohol, imidazolidinyl urea, 1,3-bis (hydroxymethyl)-5,5-dimethyl-2,3-imidazolidinedione (e.g., DMDM Hydantoin, known as GLYDANT, Lonza, Fairlawn, N.J., USA.), methylchloroisothiazolinone and methylisothiazolinone (e.g., Kathon, Rohm & Haas Co., Philadelphia, Pa., USA), methyl paraben, propyl paraben, phenoxyethanol, and sodium benzoate, phenoxyethanol, ethylhexylglycerin, Chlorphenesin, dehydroacetic acid, and mixtures thereof.

EXAMPLES

The following examples are presented to illustrate presently preferred practice thereof. As illustrations they are not intended to limit the scope of the invention. All quantities are in weight %.

Example 1

Sucrose Adhesive Composition without Conjugate

Ingredients. (1) Diglycerol 10.0 (2) Water 19.0 (3) Sucrose 70.0 (4) Preservative 1.0. Procedure. Mix (2) to (4) and heat at 90 to 95 C. for 30 to 45 minutes to a clear liquid. Add (1) and mix. Cool to room temperature. A clear, light amber sticky mobile liquid is obtained.

Example 2

Preparation of Sucrose—Polyhydroxy Lactone Conjugate Composition

Ingredients. (1) Diglycerol 10.0 (2) Water 17.0 (3) Sucrose 70.0 (4) Preservative 1.0 (5) Gluconolactone 2.0. Procedure. Mix (2) to (5) and heat at 90 to 120 C. for 30 to 45 minutes to a clear liquid. Add (1) and mix. Cool to room temperature. A clear, light amber mobile sticky liquid is obtained.

Example 3

Adhesive Power Testing

The compositions from Example 1 and Example 2 were tested for their adhesive power strength by the measurement of mechanical force required to pull apart two paper sheets coated with the same amount of test materials. The composition from Example 2 required more than twice the force, compared to composition from Example 1.

Example 4

Adhesive Composition

Ingredients. (1) Diglycerol 10.0 (2) Sucrose 87.0 (3) Gluconic acid (50% solution in water) 2.0 (4) Preservative 1.0. Procedure. Mix (2) to (4) and heat at 90 to 120 C. for 30 to 45 minutes to a clear liquid. Add (1) and mix. Cool to room temperature. A clear, light amber mobile sticky liquid is obtained.

Example 5

Adhesive Composition

Ingredients. (1) Glycerin 10.0 (2) Water 12.0 (3) Sucrose 75.0 (4) Preservative 1.0 (5) Gluconic acid 2.0. Procedure. Mix (2) to (5) and heat at 90 to 120 C. for 30 to 45 minutes to a clear liquid. Add (1) and mix. Cool to room temperature. A clear, light amber mobile sticky liquid is obtained.

Example 6

Adhesive Composition

Ingredients. (1) Diglycerol 30.0 (2) Water 8.0 (3) Sucrose 59.0 (4) Preservative 1.0 (5) Gluconic acid (50% water solution) 2.0. Procedure. Mix (2) to (5) and heat at 90 to 120 C. for 30 to 45 minutes to a clear liquid. Add (1) and mix. Cool to room temperature. A clear, light amber mobile sticky liquid is obtained.

Example 7

Adhesive Composition with Sucrose Derivatives

Ingredients. (1) Sorbitol 10.0 (2) Sucrose 60.0 (3) Preservative 1.0 (4) Gluconic acid (50% water solution) 2.0 (5) Water 10.0 (6) Diglycerol 17.0. Procedure. Mix all components and heat at 90 to 130 C. for 30 to 45 minutes to a clear liquid. Cool to room temperature. A clear, light amber mobile sticky liquid is obtained.

Example 8

Depilatory Composition

Ingredients. (1) Diglycerol 30.0 (2) Sucrose 59.0 (3) Gluconolactone 1.0 (4) Preservative 1.0 (5) Water 9.0. Procedure. Mix (2) to (5) and heat at 90 to 120 C. for 30 to 45 minutes to a clear liquid. Add (1) and mix. Cool to room temperature. A clear, light amber mobile sticky liquid is obtained.

Example 9

Adhesive Composition with Polyglycerol

Ingredients. (1) Polyglycerol 10.0 (2) Sucrose 75.0 (3) Gluconolactone 1.0 (4) Preservative 1.0 (5) Water 13.0. Procedure. Mix (2) to (5) and heat at 90 to 120 C. for 30 to 45 minutes to a clear liquid. Add (1) and mix. Cool to room temperature. A clear, light amber mobile sticky liquid is obtained.

Example 10

Consumer Testing of Compositions of Example 1, Example 2 and Example 6

A six person panel, all female, tested the compositions of Examples 1, 2, and 6 of the present invention by their direct application on skin and also the application of the product first on fabric pieces, then the application of such coated fabric pieces on skin for depilation. No dry-down period was observed. Procedure: (1) Hair should be at least ¼" long for the test. (2) Squeeze test composition, out of tube, directly onto non-woven depilatory strip. (3) With an appropriate applicator, spread test composition in an even, thin, layer onto strip. (4) Place pre-coated strip onto desired treatment area of skin. (5) Gently rub the top of strip in the direction of hair growth. (6) Once strip seems secure (5 to 10 seconds), hold skin taut, and with the other hand grasp the edge of the coated depilatory strip. (7) With a quick, but nice and even motion, remove wax strip, pulling in the opposite direction of hair growth.

The ratings, based on ease of product application, completeness of hair removal in a single treatment, ease of cleanup after use, and amount of skin irritation, from most preferred to least preferred, follow: Example 6>Example 2>>>Example 1.

Example 11

Stability Testing of Compositions of Example 1, Example 2 and Example 6

The samples of these compositions were placed in open glass jars (no lids), which were placed in an oven at 50 C. for one week. No crystallization was noted for Example 2 and 6. Complete crystallization was noted for Example 1.

Example 12

Water Washable Depilatory Composition with Emolliency

Ingredients. (1) Diglycerol 30.0 (2) Sucrose 58.0 (3) Gluconic acid (50% solution in water) 2.0 (4) Amodimethicone (and) Trideceth-12 (and) Cetrimonium Chloride 1.0 (5) Preservative 1.0 (6) Water 8.0. Procedure. Mix (2) to (6) and heat at 90 to 120 C. for 30 to 45 minutes to a clear liquid. Add (1) and mix. Cool to room temperature. A clear, mobile sticky liquid is obtained.

Example 13

Water Washable Depilatory Clay Composition

Ingredients. (1) Diglycerol 10.0 (2) Sucrose 75.0 (3) Gluconic acid (10% solution in water) 10.0 (4) Preservative 1.0 (5) White Clay 4.0. Procedure. Mix (2) to (4) and heat at 90 to 120 C. for 30 to 45 minutes to a clear liquid. Add (1) and (5) and mix. Cool to room temperature. An opaque mobile liquid is obtained.

Example 14

Depilatory and Skin Refining Facial Clay Composition with Divinylbenzene/Methacrylic Acid Copolymer Ingredients. (1) Diglycerol 10.0 (2) Sucrose 74.0 (3) Gluconolactone (10% solution in water) 10.0 (4) Preservative 1.0 (5) Divinylbenzene/methacrylic acid copolymer 1.0 (6) Zeolite 4.0. Procedure. Mix (2) to (5) and heat at 90 to 120 C. for 30 to 45 minutes to a clear liquid. Add (1) and (6) and mix. Cool to room temperature. An opaque mobile sticky liquid is obtained.

BRIEF DESCRIPTION OF DRAWINGS

FIG. 1 Chemical Structure of Hydroxy and Polyhydroxy Lactones.

What is claimed is:

1. A cosmetic adhesive composition consisting of the saccharide polyhydroxy acid ester produced by a process consisting of: (1) mixing a saccharide, a minimum quantity of water to dissolve said saccharide, and a polyhydroxy lactone, (2) heating to a temperature of 90 to 120 degrees Celsius for 30 to 45 minutes, (3) adding a water-soluble hydroxylic or polyhydroxyl solvent selected from the group consisting of diglycerol, polyglycerol, triglycerol, tetraglycerol, pentaglycerol, hexaglycerol, glycerin, polyethylene glycol, propylene glycol, butylene glycol, methylpropanediol, ethoxydiglycol, and combinations thereof, and (4) allowing the resulting product to cool to room temperature; wherein said saccharide is selected from the group consisting of sucrose, lactose, maltose, trehalose, glucose, erythrose, threose, arabinose, ribose, ribulose, xylose, xylulose, lyxose, allose, altrose, fructose, galactose, gulose, idose, mannose, sorbose, talose, tagatose, and sedoheptulose, and wherein said polyhydroxy lactone is selected from the group consisting of gluconolactone, erythronolactone, isocitric acid lactone, glucooctanolactone, galactonolactone, gulonolactone, sugar lactone, mannonolactone, saccharolactone, glucoronolactone, and ribolactone.

2. The composition of claim 1, wherein said saccharide is sucrose.

3. The composition of claim 1, wherein said polyhydroxy lactone is gluconolactone.

4. The composition of claim 1, wherein the composition is contained in dispensing applicators selected from the group consisting of roll-on, glide-on, push-up, heated containers, jars, and tubes.

5. The composition of claim 1, wherein the composition is a coating on a surface selected from the group consisting of fabric, paper, plastic, and combinations thereof.

6. The composition of claim 1, wherein (i) the saccharide is sucrose present from about 10% to 85% by weight of the composition, and wherein (ii) the water is present from about 2% to 30% by weight of the composition, and wherein (iii) the polyhydroxy lactone is gluconolactone present from about 0.1% to 10% by weight of the composition.

7. The composition of claim 1, wherein (i) the saccharide is sucrose present from about 10% to 85% by weight of the composition, and wherein (ii) the water is present from about 2% to 30% by weight of the composition, and wherein (iii) the polyhydroxy lactone is gluconolactone present from about 0.1% to 10% by weight of the composition, and wherein (iv) the water-soluble hydroxylic or polyhydroxyl solvent is diglycerol present in 2% to 30% by weight of the composition.

8. A method of removing hair from human skin comprising applying a composition of claim 1 to human skin, allowing the composition to adhere to hair, and removing the composition and hair from human skin.

9. The method of claim 8, wherein the composition is applied in strips selected from fabric strips, paper strips, plastic strips, or combinations thereof.

* * * * *